(12) United States Patent
Coutard

(10) Patent No.: US 12,702,308 B2
(45) Date of Patent: Aug. 11, 2026

(54) DEVICE FOR PHYSIOLOGICAL MEASUREMENTS, AND ASSOCIATED SET-UP METHOD

(71) Applicant: MATRIX, Nice (FR)

(72) Inventor: Patrice Coutard, Collonges Au Mont d'Or (FR)

(73) Assignee: MATRIX, Nice (FR)

( * ) Notice: Subject to any disclaimer, the term of this patent is extended or adjusted under 35 U.S.C. 154(b) by 412 days.

(21) Appl. No.: 18/572,927

(22) PCT Filed: Jun. 22, 2022

(86) PCT No.: PCT/FR2022/051215
§ 371 (c)(1),
(2) Date: Apr. 29, 2024

(87) PCT Pub. No.: WO2022/269192
PCT Pub. Date: Dec. 29, 2022

(65) Prior Publication Data

US 2024/0366094 A1 Nov. 7, 2024

(30) Foreign Application Priority Data

Jun. 23, 2021 (FR) ...................................... 2106678

(51) Int. Cl.
*A61B 5/0205* (2006.01)
*A61B 5/00* (2006.01)
(Continued)

(52) U.S. Cl.
CPC ........ *A61B 5/02055* (2013.01); *A61B 5/0002* (2013.01); *A61B 5/117* (2013.01);
(Continued)

(58) Field of Classification Search
CPC ... A61B 5/02055; A61B 5/0002; A61B 5/117; A61B 5/742; A61B 5/01; A61B 5/021;
(Continued)

(56) References Cited

U.S. PATENT DOCUMENTS

| | | | |
|---|---|---|---|
| 6,705,990 B1 * | 3/2004 | Gallant | G16H 40/63 600/490 |
| 2009/0137882 A1 * | 5/2009 | Baudino | G16H 20/00 600/300 |

(Continued)

FOREIGN PATENT DOCUMENTS

| | | |
|---|---|---|
| CN | 104771154 | 12/2017 |
| EP | 3153145 | 4/2017 |

(Continued)

OTHER PUBLICATIONS

International Search Report (with English Translation) and Written Opinion (with English translation) for PCT/FR2022/051215, dated Sep. 26, 2022, 13 pages.

*Primary Examiner* — Andrey Shostak
(74) *Attorney, Agent, or Firm* — Tucker Ellis LLP

(57) ABSTRACT

The invention relates to a medical remote consultation device (10*a*) including:
- a shell supporting a seat (12) and forming left (14) and right arm rests;
- a central unit (15) incorporated into the inside of the shell; and
- a set of sensors disposed on the left and right arm rests, the sensors being connected to the central unit;

the shell being made of two removable parts (20-21):
- a first part (20) forming the right arm rest, supporting the seat and at least four other sensors and containing the central unit; and
- a second part (21) forming the left arm rest (14) and supporting at least one blood pressure sensor (16*h*)

(Continued)

such that the installation of the medical remote consultation device can be carried out by securing the two parts (20-21) of the shell and by connecting the at least one blood pressure sensor (16*h*) to the central unit.

10 Claims, 6 Drawing Sheets

(51) Int. Cl.

| | |
|---|---|
| ***A61B 5/117*** | (2016.01) |
| *A61B 5/01* | (2006.01) |
| *A61B 5/021* | (2006.01) |
| *A61B 5/0537* | (2021.01) |
| *A61B 5/085* | (2006.01) |
| *A61B 5/087* | (2006.01) |
| *A61B 5/12* | (2006.01) |
| *A61B 5/145* | (2006.01) |
| *A61B 5/28* | (2021.01) |
| *A61B 7/02* | (2006.01) |

(52) U.S. Cl.

CPC .......... *A61B 5/6888* (2013.01); *A61B 5/6891* (2013.01); *A61B 5/742* (2013.01); *A61B 5/01* (2013.01); *A61B 5/021* (2013.01); *A61B 5/0537* (2013.01); *A61B 5/085* (2013.01); *A61B 5/087* (2013.01); *A61B 5/121* (2013.01); *A61B 5/14542* (2013.01); *A61B 5/28* (2021.01); *A61B 7/02* (2013.01); *A61B 2560/0406* (2013.01); *A61B 2560/0443* (2013.01); *A61B 2560/0462* (2013.01); *A61B 2562/0247* (2013.01); *A61B 2562/0271* (2013.01)

(58) Field of Classification Search

CPC ....... A61B 5/0537; A61B 5/085; A61B 5/087; A61B 5/121; A61B 5/14542; A61B 5/28; A61B 7/02; A61B 2560/0406; A61B 2560/0443; A61B 2560/0462; A61B 2562/0247; A61B 2562/0271; A61B 5/0064; A61B 5/0077; A61B 5/12; A61B 5/14551; A61B 5/318; A61B 5/441; A61B 5/0205; A61B 5/7465

See application file for complete search history.

(56) References Cited

U.S. PATENT DOCUMENTS

| | | | | |
|---|---|---|---|---|
| 2019/0095957 | A1* | 3/2019 | Ibarria | G16H 10/20 |
| 2021/0153753 | A1* | 5/2021 | Naude | A61B 5/14542 |

FOREIGN PATENT DOCUMENTS

| | | | | |
|---|---|---|---|---|
| EP | 3420892 | | 1/2019 | |
| FR | 3041876 | A1 * | 4/2017 | A61G 15/125 |

* cited by examiner

10b

DEVICE FOR PHYSIOLOGICAL MEASUREMENTS, AND ASSOCIATED SET-UP METHOD

FIELD OF THE INVENTION

This invention relates to the technical field of the taking of physiological measurements independently or semi-independently, i.e. with or without the assistance of a physical person, present or remote. The invention enables the performing of a medical self-diagnosis and/or the implementation of a medical remote consultation while interacting with a practitioner.

More specifically, the invention relates to a physiological measurement device allowing the integration of a large number of sensors into a contained environment. The invention also relates to the method of installation of such a device.

The small dimensions of the physiological measurement device of the invention make it possible to envision many applications, for example to form a remote consultation room in a place open to the public, such as a town hall, or a private space, such as a retirement home, and to facilitate the accessibility of a remote consultation. Moreover, the small dimensions of the physiological measurement device can allow its incorporation into a drone, a land vehicle, a ship or any other vehicle.

PRIOR ART

The increasing development of remote consultation systems makes it possible to simplify access to medical care. For example, remote consultation systems make it possible to combat local shortages of medical professionals and allow simplified access to medical care, particularly emergency medical care.

To carry out medical remote consultations, a large number of mobile applications exist allowing a practitioner to talk with a patient. These applications are limited since they do not make it possible to obtain controlled physiological measurements allowing a practitioner to establish a reliable diagnosis.

Remote consultation or self-diagnosis terminals also exist. These terminals conventionally include a screen and a camera used to interact with a practitioner or a software program used to guide a patient to allow him to carry out a self-diagnosis.

On either side of this screen, the patient can interact with a set of sensors, such as a dermatoscope, an otoscope, an oximeter, a stethoscope, a tensiometer or a thermometer.

During a remote consultation or a self-diagnosis, the practitioner or the software may ask the patient to use several sensors in succession to establish a diagnosis. This diagnosis phase can last several long minutes during which the patient is often sitting on a chair in front of the terminal and he must periodically move to reach one or the other of the sensors.

In a variant, to simplify the accessibility of the sensors and improve privacy, there are also remote consultation booths, such as the "AI POD" product of the Applicant or as described in the document EP 3 420 892. These booths conventionally include a seat on which the patient is intended to sit and a screen placed facing the seat.

More specifically, these remote consultation booths aim to maximize the number of measurements which can be taken in a minimum of time, a factor of the quality of the remote consultation or the self-diagnosis. For example, the above-mentioned "AI POD" product currently allows the acquisition of 26 physiological measurements in 6 minutes.

To obtain this type of measurement-taking speed, booths conventionally make provision for disposing the physiological sensors around the seat on which the patient is intended to take up position, such as to simplify access to each sensor. To do so, the remote consultation booths generally use a shell supporting the seat and the screen placed facing the seat. This shell is formed by a double wall containing a central unit to which all the physiological sensors are connected. Thus, the physiological sensors are placed around the seat of the cabin and the connectors of these sensors enter through openings in the shell before being connected to the central unit.

However, existing solutions do not make it possible to obtain a booth of small dimensions since the shell is of necessity quite bulky to support the seat, the screen and the set of sensors, and contain the central unit and the different connectors of the sensors.

It follows that these booths conventionally have minimum dimensions of approximately 3 meters in length by 1.5 meters in height. These imposing dimensions do not allow these booths to be incorporated into all spaces. For example, these booths cannot pass through a standard door, of a width of less than 1 meter.

As a result the existing solutions have either a limited measurement-taking quality and privacy level, as is the case for terminals, or large dimensions and corresponding difficulties of installation, as is the case for booths.

The technical problem of the invention is to obtain a physiological measurement device allowing rapid access to a large number of sensors with improved installability.

SUMMARY OF THE INVENTION

To meet this technical problem, the invention makes provision for a physiological measurement device with a shell including at least two removable parts: a first part supporting the seat and a large number of sensors and containing the central unit; and a second part mainly supporting a blood pressure sensor.

The screen can be incorporated into a third part of the shell such that the assembly of the three parts of the shell forms a booth with the screen placed facing the seat. In a variant, the screen can be attached facing the seat without being mechanically connected to the seat, typically to fashion a remote consultation or self-diagnosis space.

For example, to fashion a remote consultation room in an existing public or private space, the screen can be attached to a wall. The shell is then transported and installed in front of the screen by moving the two parts of the shell in succession and by passing through standard doors.

The discovery of the possibility of separating the elements of the shell to obtain a removable shell of at least two parts is particularly surprising given the overall dimensions of the sensors and of the connectors of existing booths. It has been found that, to guarantee both the ease of installation and accessibility of the different sensors, the shell has to be split into two very different parts, differing both in shape and in the number of types of sensors they support.

For this purpose, according to a first aspect, the invention relates to a remote consultation device including: a shell supporting a seat and forming left and right arm rests; a central unit incorporated into the inside of the shell; and a set of sensors disposed on the left and right arm rests, the sensors being connected to the central unit through openings in the shell.

The invention is characterized in that the shell is made of two removable parts:

a first part forming the right arm rest, supporting the seat and at least four other sensors and containing the central unit; and a second part forming the left arm rest and supporting at least one blood pressure sensor such that the installation of the medical remote consultation device can be carried out by securing the two parts of the shell and by connecting the at least one blood pressure sensor to the central unit.

Within the meaning of the invention, the left arm rest is the arm rest present on the left of the seat and allowing the patient sitting on the seat to rest his left arm when the two parts of the shell are assembled. Similarly, the right arm rest corresponds to the arm rest present on the right of the seat and allowing the patient sitting on the seat to rest his right arm when the two parts of the shell are assembled.

The solution of the invention consisting in positioning the blood pressure sensor on the left arm rest is not trivial since the blood pressure measurements are more accurate when they are taken from the left arm, i.e. from the arm nearest the heart. Moreover, blood pressure sensors used to obtain accurate measurements are often bulkier than other sensors that can be disposed on the arm rests, such as dermatoscopes, otoscopes, oximeters, stethoscopes, tensiometers or thermometers.

Thus, by mainly supporting the blood pressure sensor on the second removable part forming the left arm rest, it is possible to detach bulky elements, such as the left arm rest and the blood pressure sensor, while limiting the complexity of assembly of the two parts of the shell. Specifically, the detachment of the shell into several parts causes complications during the assembly of the shell, particularly when connecting the sensors present in the part that does not contain the central unit since these sensors may not be connected to the central unit before transportation.

The positioning of the bulkiest sensor able to be disposed on the arm rests in the part not containing the central unit has made it possible to simplify transportation and installation while limiting complications during the assembly of the shell. Specifically, it is now possible to obtain two parts of the shell, the dimensions of which are less than 1 m, thus allowing the passing of the different parts of the medical remote consultation device through standard doors.

Moreover, the blood pressure sensor is not the bulkiest sensor which can be incorporated into the medical remote consultation since it may be desirable to incorporate a weighing scale or else a patient height sensor. Preferably, these sensors are also supported by the first part forming the right arm rest such that they can be connected to the central unit before the transportation and the installation of the first part.

Thus, the invention does not make provision for simply incorporating the bulkiest sensor into a removable part but more specifically for incorporating the bulkiest sensor which can be placed on an arm rest so as to detach both the structure forming the arm rest and this sensor. Of course, other sensors can also be placed on the second part forming the left arm rest in addition to the blood pressure sensor. To simplify the connection of several sensors placed on the removable part of that containing the central unit, a connection harness can be formed for all of these sensors in order to simplify their connections to the central unit.

To obtain a large number of measurements and simplify the installation, the first part forming the right arm rest supports a body composition sensor, an oximeter, an audiometer, an electrocardiogram, an ultrasound device, an otoscope, a stethoscope, a spirometer, a dermatoscope, an ultrasound device and a vision scanner.

The oximeter is conventionally used to obtain the level of saturation of oxygen in the blood. Moreover, the central unit can include electronic processing, for example for extracting the heart rate or else blood stiffness based on the measurement of the oximeter.

Preferably, the body composition sensor is a hand-to-foot sensor used to obtain particularly reliable information over the whole body, not only as regards the level of body fat of the patient but also his muscle mass, his intracellular extracellular hydration etc.

Besides the sensors incorporated into the shell, sensors can be incorporated into the screen or into an access terminal for accessing a space containing the seat and the screen.

In the latter example, the remote consultation device also includes an access terminal, intended to be attached to the entrance of a space in which the screen and the seat are installed, the terminal including means of identification and a temperature sensor.

This embodiment makes it possible to take the patient's temperature, for example by means of an infrared sensor, when the patient accesses the remote consultation space. For example, the access to the remote consultation space can be controlled by an access card, biometric recognition means or any other identification means.

The set of sensors incorporated into the shell, the access terminal and optionally the screen make it possible to form a remote consultation room out of an existing room.

To do this, according to a second aspect, the method of installation of the medical remote consultation device according to the first aspect of the invention includes the following steps:

movement of the first part of the shell into a room;

movement of the second part of the shell into the room;

attachment of the second part onto the first part of the shell;

connection of the at least one blood pressure sensor to the central unit;

incorporation of a screen into the room; and connection of the screen with the central unit.

Preferably, to attach the second part of the shell to the first part thereof, the shell includes mechanical poka-yoke devices interacting between the two parts of the shell.

Moreover, to ensure the attachment of the two parts of the shell, an access hatch can be fashioned behind the seat of the first part of the shell. This access hatch makes it possible to access the central unit to connect the at least one blood pressure sensor, and it also makes it possible to bolt both parts of the shell to ensure durable attachment.

BRIEF DESCRIPTION OF THE FIGURES

The invention will be clearly understood on reading the following description, the details of which are given solely by way of example, and described with reference to the appended figures, in which identical reference numbers pertain to identical elements.

DETAILED DESCRIPTION OF THE INVENTION

The following description illustrates two separate embodiments: a first embodiment of a remote consultation device 10*a* used to fashion an enclosed space, such as a room reserved for remote consultation in a town hall; and a second embodiment of a remote consultation device 10*b* taking the form of a booth. In these two embodiments, a shell 11*a*-11*b* is formed around a seat 12 and has a double partition such as to support and contain the electrical and electronic power supply and control elements of a set of sensors 16*a*-16*h*.

Figure 1:
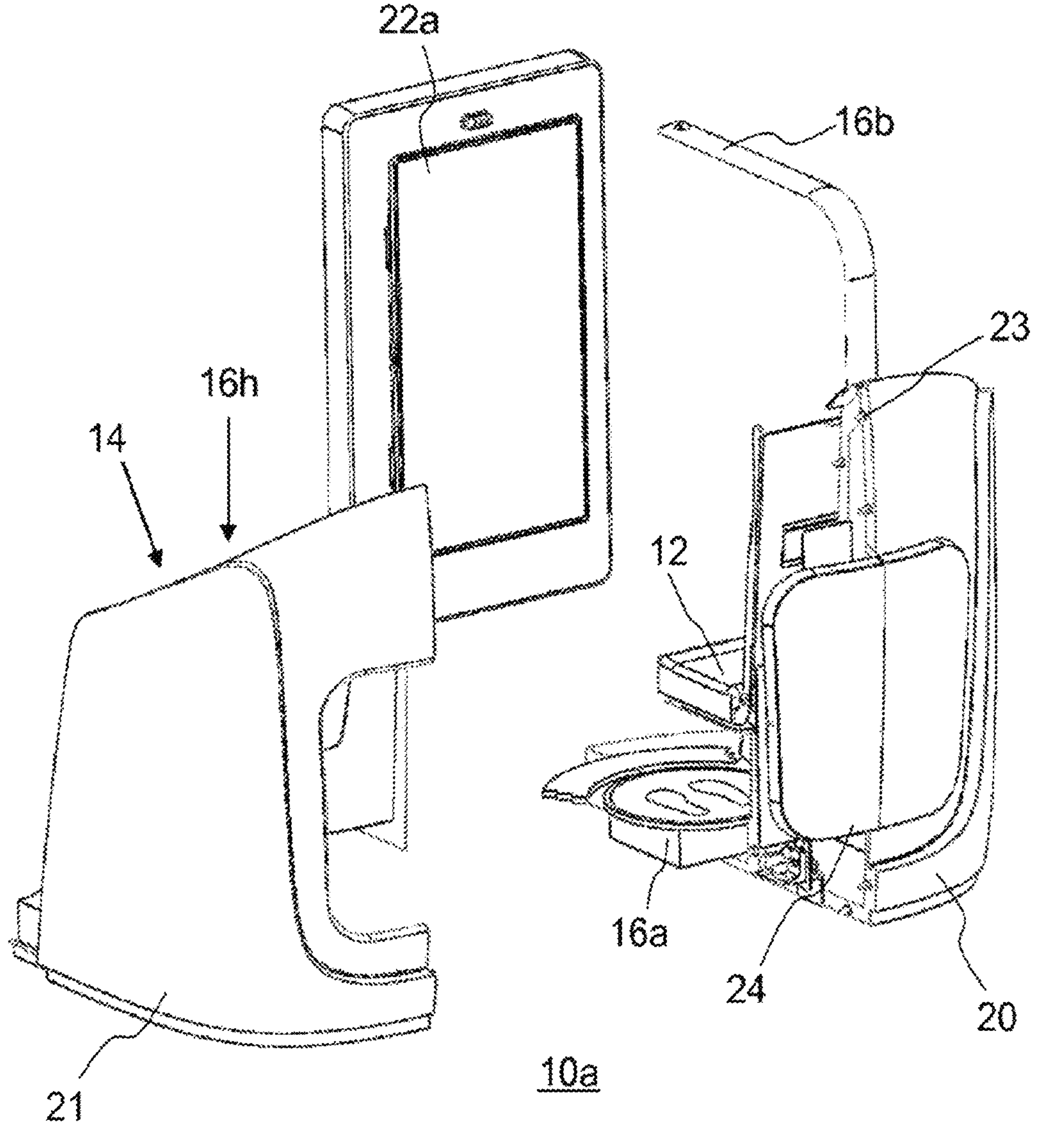
FIG. 1 illustrates an exploded perspective view of a medical remote consultation device according to a first embodiment of the invention.
Figure 2:
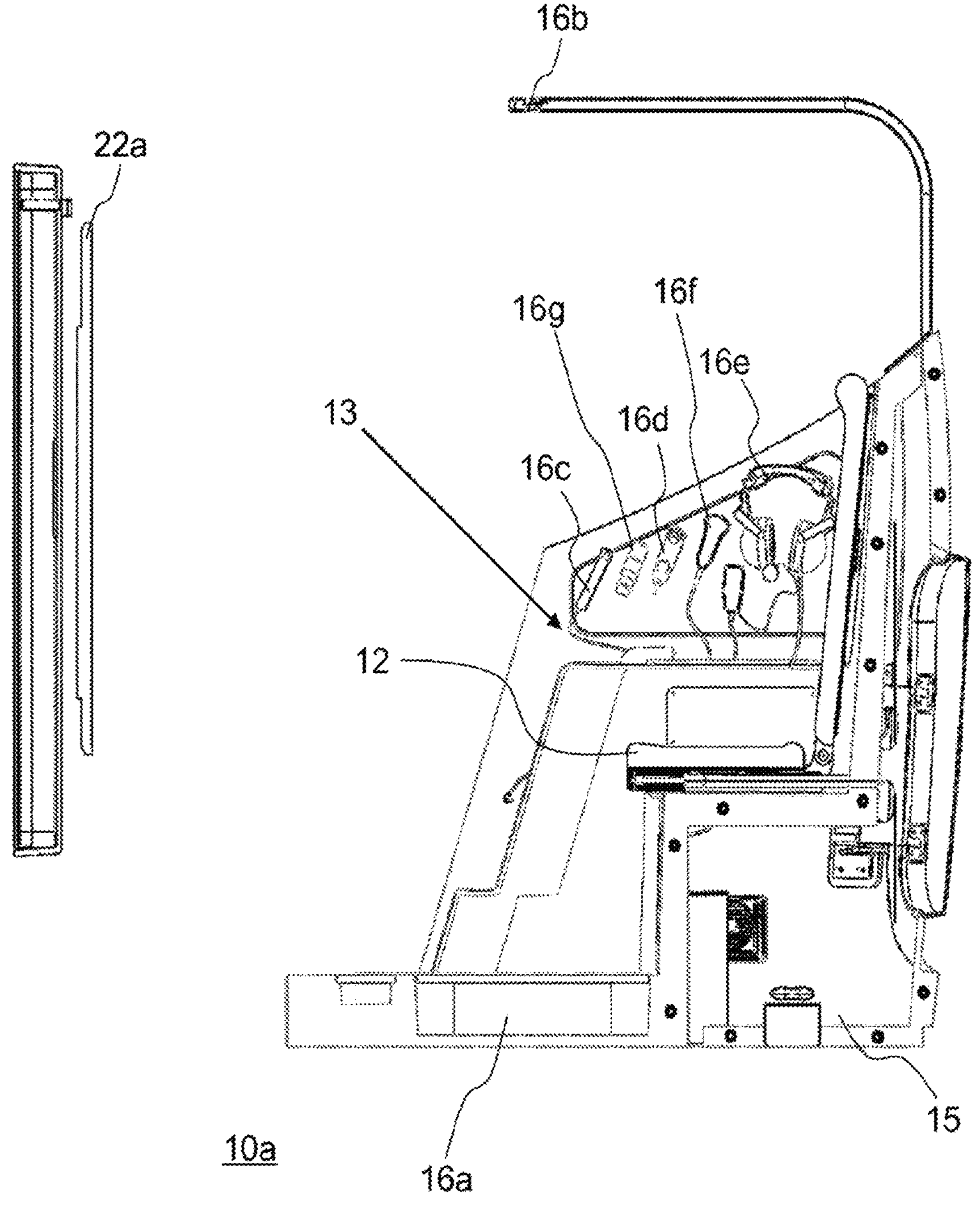
FIG. 2 illustrates a side section view of the medical remote consultation device of FIG. 1.
Figure 3:
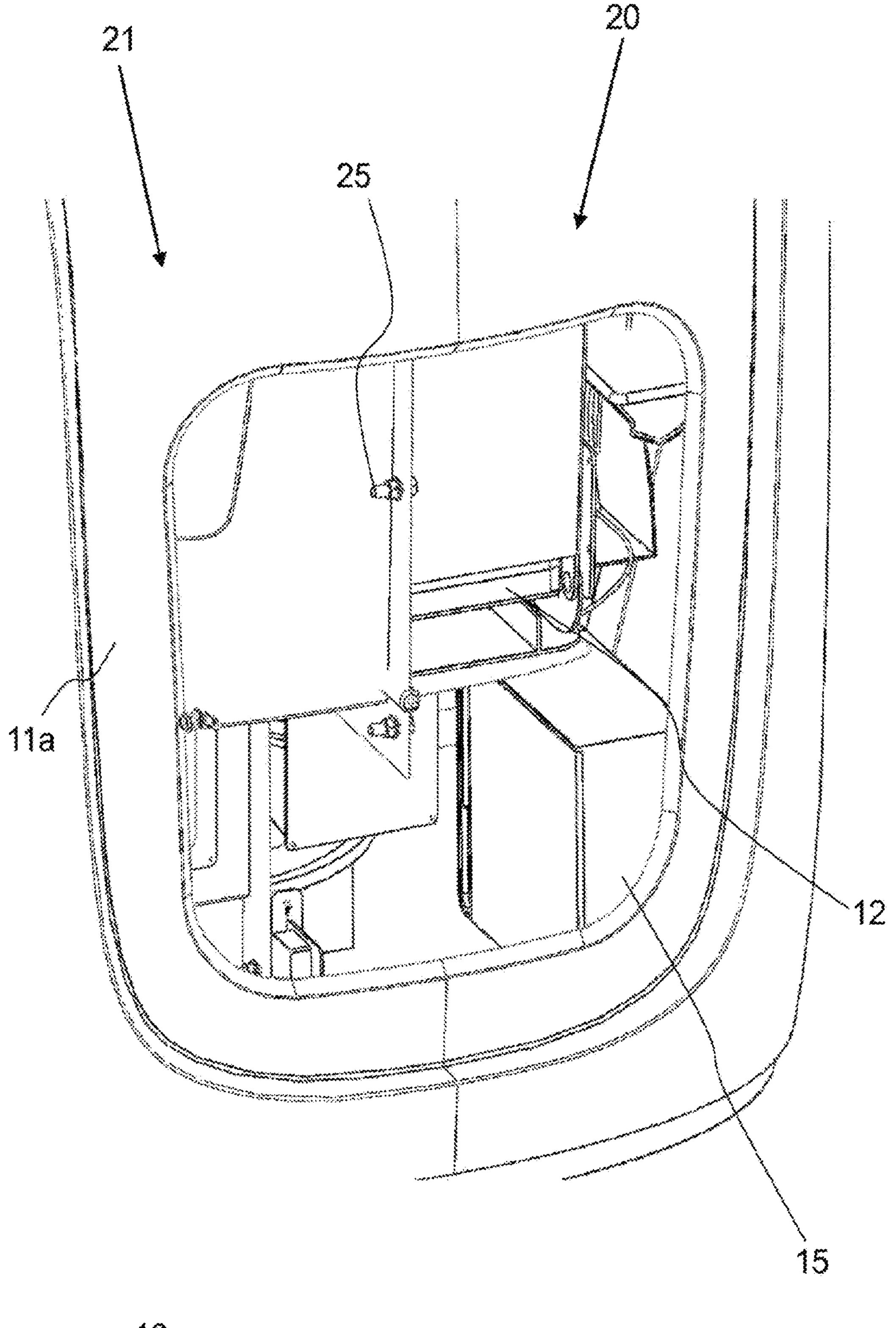
FIG. 3 illustrates a perspective view of a maintenance access hatch fashioned behind a seat of the medical remote consultation device of FIG. 1.

In the first embodiment, illustrated in FIGS. 1 to 3, the shell 11*a* is made of two removable parts 20-21 while the screen 22*a* is positioned facing a seat 12 containing the first part 20. According to the invention, the first part 20 forms the right arm rest 13 and supports the seat 12 whereas the second part 21 forms the left arm rest 14.

Moreover, a blood pressure sensor 16*h* is disposed on the left arm rest 14 of the second part 21 in order to measure the blood pressure of the patient when he is sitting on the seat 12.

Other sensors can also be disposed on the left arm rest 14 so that the patient can reach them easily. Preferably, the most of the sensors 16*a*-16*g* are disposed on the right arm rest 13, as illustrated in FIG. 2. For example, several sensors may be accessible above the right arm rest 13, such as an oximeter 16*d*, an audiometer 16*e*, an electrocardiogram 16*f*, an ultrasound device 16*g*, an otoscope, a stethoscope, a spirometer, a dermatoscope, an ultrasound device and a vision scanner. Of course, other types of sensors can be used without changing the invention.

As illustrated in FIG. 2, the floor of the remote consultation device 10*a* can be formed by a weighing scale 16*a* attached to the first part 20 while the upper part of the remote consultation device 10*a* can have an incorporated patient height sensor 16*b*, also attached to the first part 20. A body composition sensor 16*c* is preferably incorporated into the first part 20, for example a hand-to-foot sensor.

According to the invention at least four sensors 16*a*-16*g* are supported by the first part 20. Specifically, it is preferable to incorporate the sensors into the first part 20 since this part 20 also contains the central unit 15 to which the sensors 16*a*-16*h* are connected. More precisely, the central unit 15 can be placed under the seat 12 behind an access hatch 24 fashioned between the seat 12 in the first part 20 of the shell. For example, this access hatch 24 can be mounted on hinges attached to the first part 20 and contain a locking mechanism.

The central unit 15 may correspond to a computer associated with a connection board for the different sensors 16*a*-16*h*. For example, a USB-type router, for a universal serial bus, can be connected to the computer to supply power and receive data from the different sensors 16*a*-16*h*. To do this, the sensors 16*a*-16*h* are connected to the central unit by means of USB cables entering the double partition through openings in the shell 11*a*.

In a variant, other types of connection can be used according to the sensors 16*a*-16*h* used.

Besides these wired connectors to the sensors 16*a*-16*h*, the central unit 15 is also connected to a screen 22*a*, wired or wireless. In the first embodiment, the screen 22*a* is attached facing the seat 12 without being mechanically connected to the seat 12. The central unit 15 can be connected to an access terminal attached to the entrance of the space in which the screen 22*a*-22*b* and the seat 12 are installed.

In the first embodiment, the access terminal can be disposed at the entrance to a room in which the seat 12 and the screen 22*a* are installed and contain means of identification and a temperature sensor.

To obtain the formation of the shell, the second part 21 is attached to the first part 20. To do this, each wall of the shell 11*a* is fitted with mechanical poka-yoke devices 23 at the level of the given connection area of the shell 11*a*. The attachment of the two parts 20-21 of the shell 11*a* can also be provided via securing means of screw/nut type 25. Preferably, plates attached to each part 20-21 are disposed facing one another with coaxial bores such as to insert the securing means of screw/nut type 25 into these bores. As illustrated in FIG. 3, these bores can be accessible in the access hatch 24.

Besides the attachment of the screw/nut-type securing means 25, the access hatch 24 also makes it possible to connect the blood pressure sensor 16*h* to the central unit 15 after attaching the two parts 20-21 of the shell 11*a*. Thus, the central unit 15 is accessible from the access hatch 24, thus making it possible to carry out maintenance operations on the central unit 15.

Besides the central unit 15, the double wall formed by the shell 11*a* also makes it possible to incorporate the electrical components used to supply power to the remote consultation device 10*a* and the network connectors.

Specifically, the central unit 15 is preferably also connected to the Internet network to interact with a computer server to ensure a secure communication between the remote consultation device 10*a* and a practitioner. This computer server can also transmit authentication information to the patient to authorize his access to the remote consultation device 10*a* and deploy any updates to the remote consultation device 10*a*.

When the patient is authorized to use the remote consultation device 10*a*, the central unit 15 communicates with the server and guides the patient for the taking of physiological measurements independently or semi-independently, i.e. with or without the assistance of a physical person, present or remote.

Figure 4:
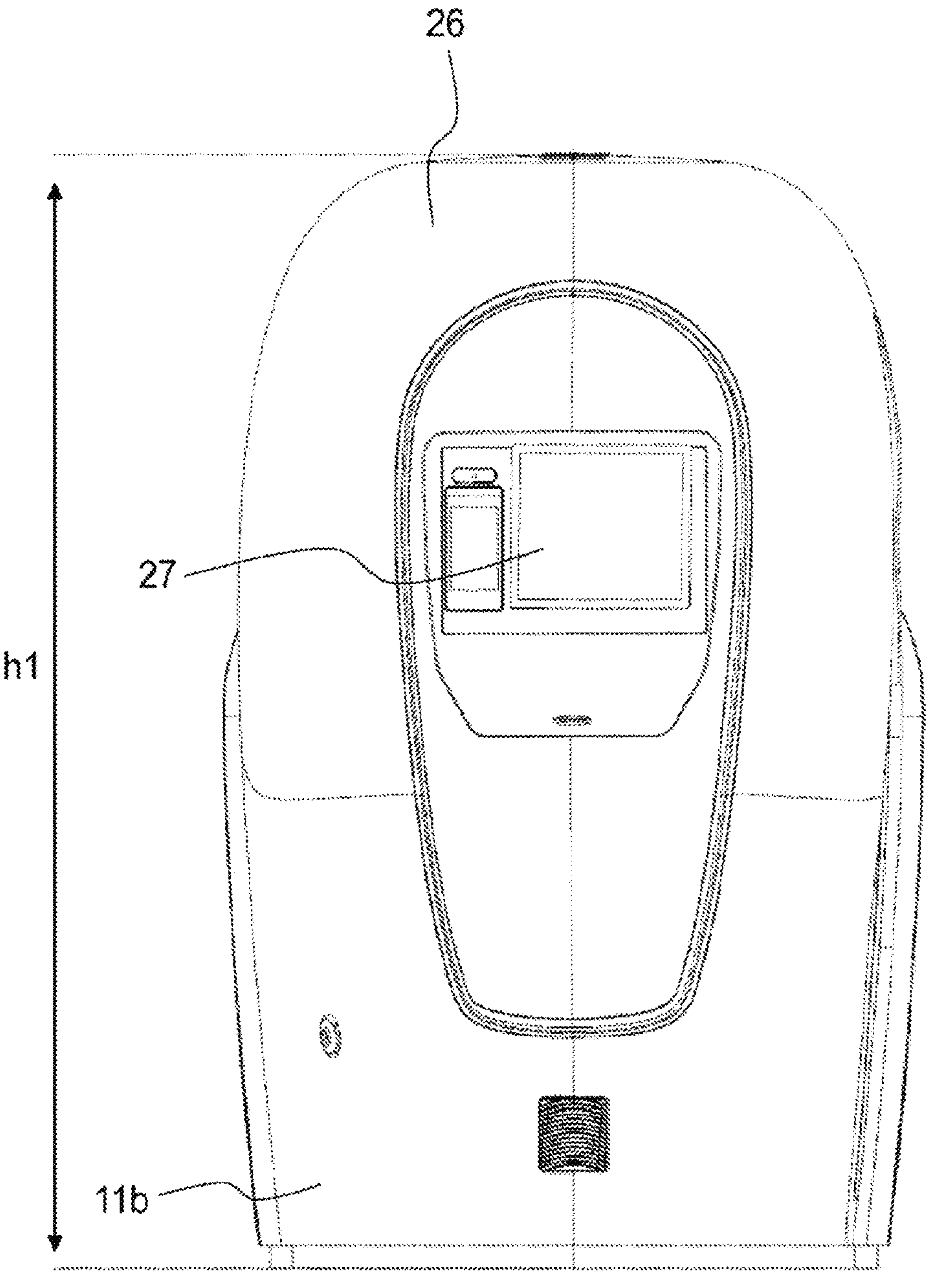
FIG. 4 illustrates a front view of a medical remote consultation device according to a second embodiment of the invention.
Figure 5:
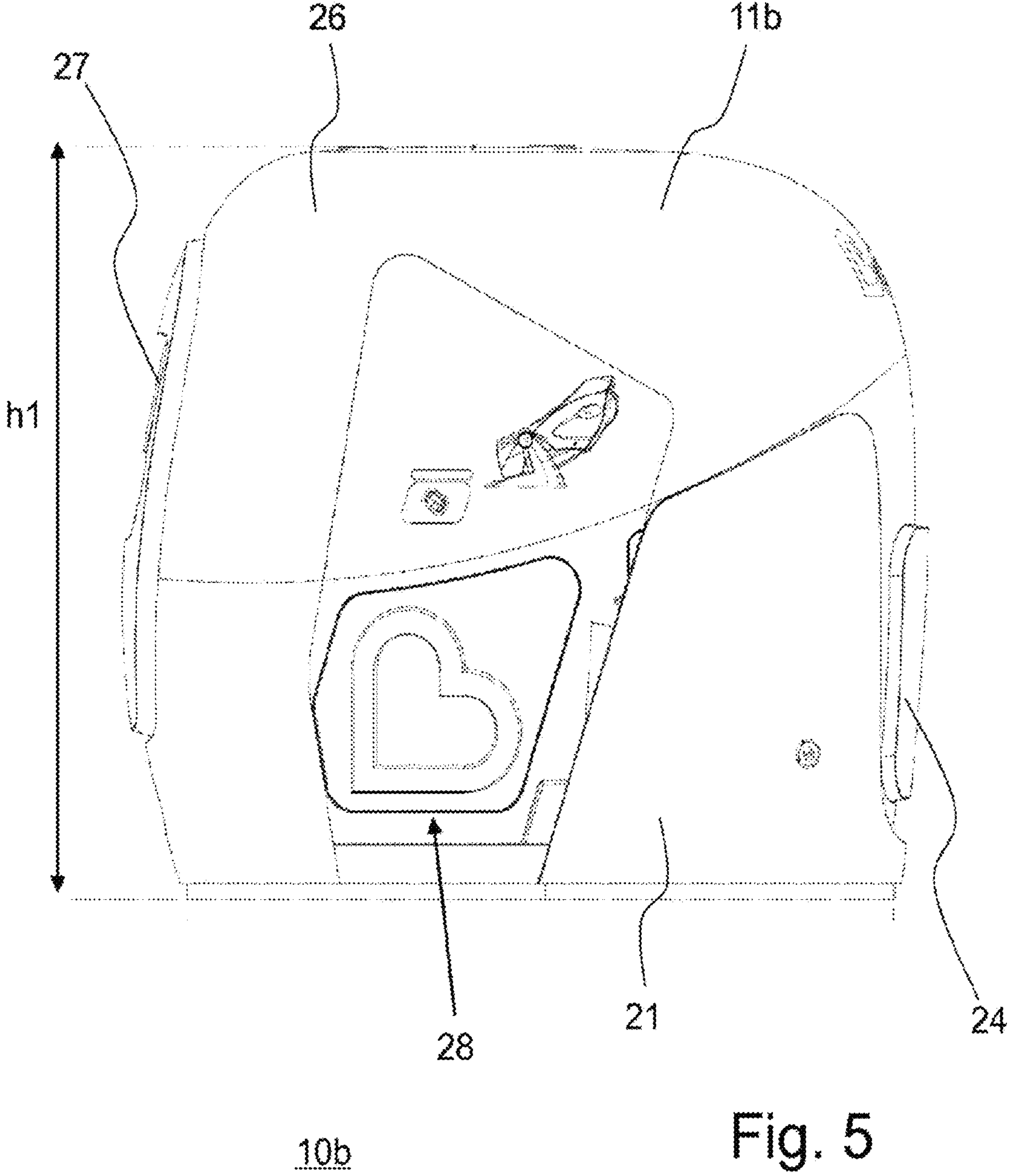
FIG. 5 illustrates a side view of the medical remote consultation device of FIG. 4.
Figure 6:
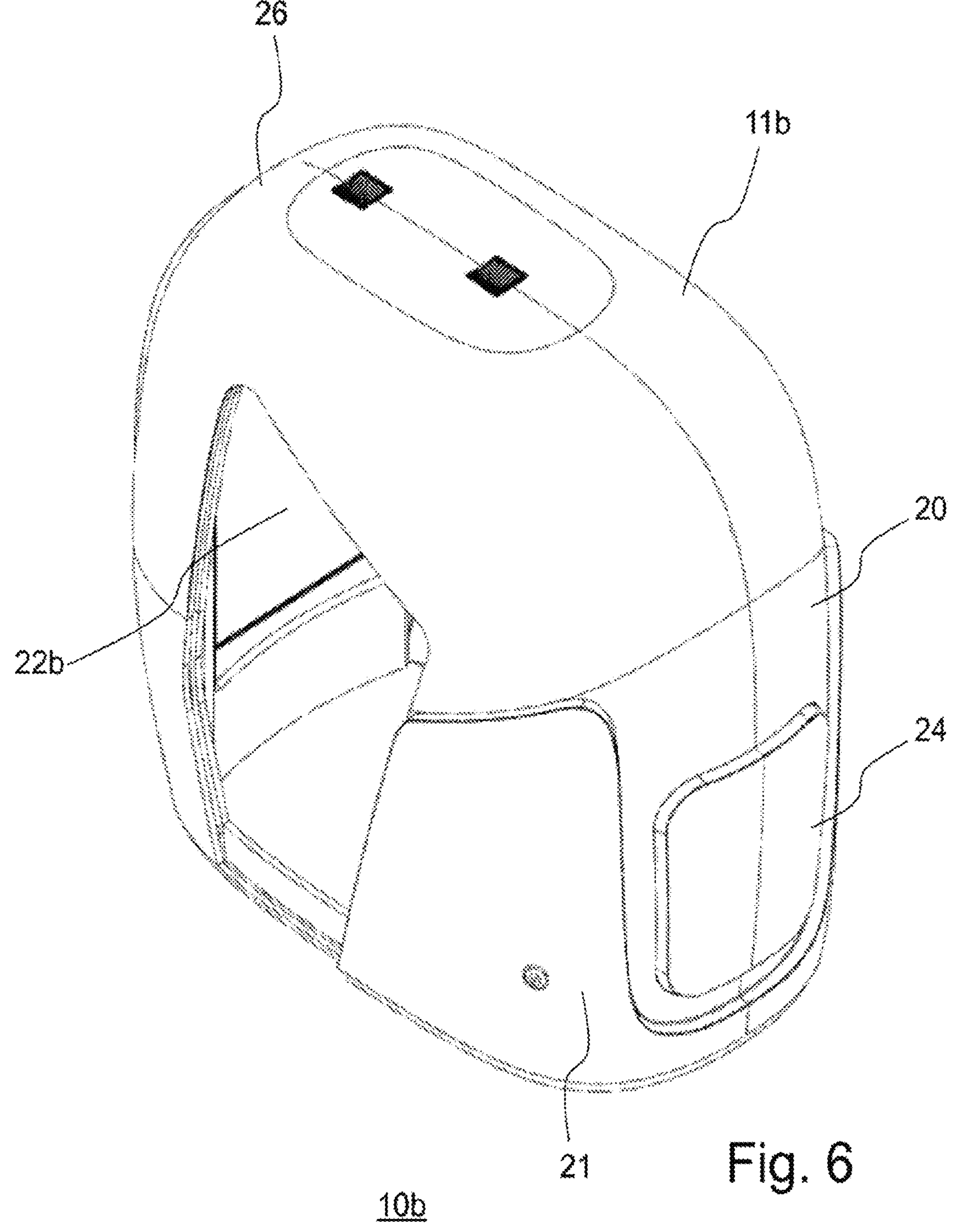
FIG. 6 illustrates a top perspective view of the medical remote consultation device of FIG. 4.

In the second embodiment, illustrated on FIGS. 4 to 6, the shell 11*b* repeats the two parts 20-21 of the first embodiment to which are added a third part 26 containing a screen 22*b* such that the assembly of the three parts 20, 21, 26 of the shell 11*b* forms a cabin with the screen placed facing the seat 12.

This third part 26 can be added and attached with all the known mechanical means. Furthermore, the screen 22*b* can be connected in a wired manner to the central unit 15.

In the second embodiment, as illustrated in FIGS. 4 and 5, the structure of the booth guarantees the privacy of the conversation by means of a removable door 28 preferably closed when the patient is installed on the seat 12. Thus, the access terminal 27 can be disposed directly on the third part 26 of the shell 11*b*.

The invention makes it possible to obtain a medical remote consultation device 10*a*-10*b* with a seat 12 around which a large number of sensors 16*a*-16*h* can be disposed and easily accessible. The seat 12 and its shell 11*a* can have dimensions in the order of 1500 to 2000 mm in length by 1300 to 1800 mm in width in the case of the first embodiment. In the second embodiment, the booth can have dimensions in the order of 2300 to 3000 mm in length by 1300 to 1800 mm in width and 2000 to 2500 mm in height hi.

Despite these large dimensions, the assembly of the shell 11*a*-11*b* in several removable parts 20, 21, 26 simplifies the installation of the medical remote consultation device 10*a*-10*b*. Moreover, the proximity of the various sensors 16*a*-16*h* allows the acquisition of 26 physiological measurements in 6 minutes.

The invention claimed is:

1. A medical remote consultation device including:

a shell supporting a seat and forming first and second arm rests;

a central unit incorporated into an inside of the shell; and a set of sensors disposed on the first and second arm rests, the sensors being connected to the central unit through openings in the shell;

the shell comprising two removable parts:

the first part forming the first arm rest, supporting the seat and at least four sensors of the set of sensors and containing the central unit; and the second part forming the second arm rest and supporting at least one blood pressure sensor such that installation of the medical remote consultation device can be carried out by securing the first and second parts of the shell and by connecting the at least one blood pressure sensor to the central unit.

2. The medical remote consultation device as claimed in claim 1, further comprising a screen configured to be attached facing the seat.

3. The medical remote consultation device as claimed in claim 1, wherein the shell also includes a third part comprising a screen such that the assembly of the three parts of the shell forms a cabin with the screen placed facing the seat.

4. The medical remote consultation device as claimed in claim 1, wherein the first part forming the first arm rest supports a weighing scale and/or a height sensor.

5. The medical remote consultation device as claimed in claim 1, wherein the first part forming the first arm rest supports a body composition sensor, an oximeter, an audiometer, an electrocardiogram, an ultrasound device, an otoscope, a stethoscope, a spirometer, a dermatoscope, and a vision scanner.

6. The medical remote consultation device as claimed in claim 5, wherein the body composition sensor is a hand-to-foot sensor.

7. The medical remote consultation device as claimed in claim 2, further comprising an access terminal configured to be attached to an entrance of a space in which the screen and the seat are installed, the access terminal including means of identification and a temperature sensor.

8. The medical remote consultation device as claimed in claim 1, wherein the shell includes mechanical poka-yoke devices interacting between the first and second parts of the shell.

9. The medical remote consultation device as claimed in claim 1, wherein the shell includes an access hatch fashioned behind the seat of the first part of the shell.

10. A method of installation of the medical remote consultation device as claimed in claim 1, the method including the following steps:

movement of the first part of the shell into a room;

movement of the second part of the shell into the room;

attachment of the second part onto the first part of the shell;

connection of the at least one blood pressure sensor to the central unit;

incorporation of a screen into the room; and connection of the screen with the central unit.

* * * * *